(12) United States Patent
Moorlag et al.

(10) Patent No.: US 10,234,342 B2
(45) Date of Patent: Mar. 19, 2019

(54) 3D PRINTED CONDUCTIVE COMPOSITIONS ANTICIPATING OR INDICATING STRUCTURAL COMPROMISE

(71) Applicant: XEROX CORPORATION, Norwalk, CT (US)

(72) Inventors: Carolyn Moorlag, Mississauga (CA); Rachel Prestayko, Hamilton (CA); Barkev Keoshkerian, Thornhill (CA); Sarah J. Vella, Milton (CA)

(73) Assignee: XEROX CORPORATION, Norwalk, CT (US)

( * ) Notice: Subject to any disclaimer, the term of this patent is extended or adjusted under 35 U.S.C. 154(b) by 376 days.

(21) Appl. No.: 15/090,259

(22) Filed: Apr. 4, 2016

(65) Prior Publication Data

US 2017/0284876 A1    Oct. 5, 2017

(51) Int. Cl.

| | |
|---|---|
| G01L 1/22 | (2006.01) |
| B33Y 10/00 | (2015.01) |
| H01B 1/24 | (2006.01) |
| H01B 1/22 | (2006.01) |
| B28B 1/00 | (2006.01) |
| B33Y 80/00 | (2015.01) |
| B33Y 70/00 | (2015.01) |
| C09D 5/24 | (2006.01) |

(Continued)

(52) U.S. Cl.
CPC ............ *G01L 1/2206* (2013.01); *B28B 1/001* (2013.01); *B29C 64/106* (2017.08); *B33Y 10/00* (2014.12); *B33Y 70/00* (2014.12); *B33Y 80/00* (2014.12); *C09D 5/24* (2013.01); *G01R 1/00* (2013.01); *H01B 1/22* (2013.01); *H01B 1/24* (2013.01); *B29K 2105/162* (2013.01); *B29K 2105/167* (2013.01); *B29K 2505/00* (2013.01); *B29K 2507/04* (2013.01); *B29K 2995/0005* (2013.01); *B82Y 30/00* (2013.01); *G01N 27/20* (2013.01)

(58) Field of Classification Search
None
See application file for complete search history.

(56) References Cited

U.S. PATENT DOCUMENTS

| | | |
|---|---|---|
| 4,769,177 A | 9/1988 | Hocker et al. |
| 5,789,680 A | 8/1998 | Fujimoto |

(Continued)

FOREIGN PATENT DOCUMENTS

| | | |
|---|---|---|
| CA | 2915409 A1 | 12/2014 |
| EP | 2 489 442 A1 | 8/2012 |

OTHER PUBLICATIONS

Prestayko et al., "Conductive Polymer Composite," U.S. Appl. No. 15/044,456, filed Feb. 16, 2016.

(Continued)

*Primary Examiner* — Peter J Macchiarolo
*Assistant Examiner* — Jermaine L Jenkins
(74) *Attorney, Agent, or Firm* — MH2 Technology Law Group LLP (57) ABSTRACT

An article includes a body and at least one 3D-printable conductive composite segment in mechanical communication with the body. The body includes a first material and the at least one conductive composite segment includes a matrix material, a plurality of carbon nanotubes, and conductive additives. The conductive additives include a plurality of metallic particulates, a plurality of graphitic particles or a combination thereof.

20 Claims, 7 Drawing Sheets

(51) Int. Cl.
    *G01R 1/00*     (2006.01)
    *B29C 64/106*     (2017.01)
    *B29K 105/16*     (2006.01)
    *B29K 507/04*     (2006.01)
    *B29K 505/00*     (2006.01)
    *B82Y 30/00*     (2011.01)
    *G01N 27/20*     (2006.01)

(56) References Cited

U.S. PATENT DOCUMENTS

| | | | |
|---|---|---|---|
| 7,925,454 | B1 | 4/2011 | Narcus |
| 8,865,604 | B2 * | 10/2014 | Wasynczuk ............ H01B 1/02 428/378 |
| 2004/0016912 | A1 | 1/2004 | Bandyopadhyay et al. |
| 2011/0028678 | A1 | 2/2011 | Matsuzono et al. |
| 2011/0260116 | A1 | 10/2011 | Plee et al. |
| 2012/0024353 | A1 | 2/2012 | Ge et al. |
| 2012/0247808 | A1 | 10/2012 | Lam |
| 2015/0123043 | A1 | 5/2015 | Nagamune et al. |
| 2016/0198576 | A1 * | 7/2016 | Lewis ............ H01L 23/49822 361/761 |
| 2017/0129170 | A1 * | 5/2017 | Kim ................. B29C 67/0055 |
| 2017/0129182 | A1 * | 5/2017 | Sauti ................ B29C 67/0085 |
| 2017/0151704 | A1 * | 6/2017 | Go ..................... B29C 47/0069 |
| 2017/0207001 | A1 * | 7/2017 | Vella ...................... H01B 1/24 |
| 2017/0267532 | A1 | 9/2017 | Liu |
| 2017/0297262 | A1 * | 10/2017 | Grigorian ............ B29C 64/153 |
| 2017/0346129 | A1 * | 11/2017 | Stolyarov ........... H01M 10/058 |
| 2018/0049655 | A1 * | 2/2018 | Melnykowycz ... A61B 5/02141 |

OTHER PUBLICATIONS

Prestayko et al., "Conductive Polymer Composite," U.S. Appl. No. 15/000,554, filed Jan. 19, 2016.
Prestayko et al., "Conductive Polymer Composite," U.S. Appl. No. 15/000,588, filed Jan. 19, 2016.
Chun et al., "High Conductive, Printable and Stretchable Composite Films of Carbon Nanotubes and Silver," Nature Nanotechnology, vol. 5, 2010, 853-857.
Office Action dated Mar. 2, 2018 from related Canadian Application No. 2,957,114.

* cited by examiner

3D PRINTED CONDUCTIVE COMPOSITIONS ANTICIPATING OR INDICATING STRUCTURAL COMPROMISE

DETAILED DESCRIPTION

Field of the Disclosure

The present disclosure is directed to smart articles comprising conductive compositions that may be utilized for indicating structural compromise or potential structural compromise.

Background

Additive manufacturing (also known as three dimensional printing) as practiced in industry has been, to date, mostly concerned with printing structural features. There is a need for materials and processes that integrate functional properties (such as electronic features) into additive manufacturing. Recently, polymeric composite compositions of conductive materials that are potentially useful in additive manufacturing have been commercialized, but their conductivities are generally low, ranging from ~$10^{-3}$ S/cm to upwards of ~2.0 S/cm. The mechanical properties of the commercially available materials, particularly the conductive materials such as Acrylonitrile butadiene styrene (ABS) or polylactic acid (PLA), are generally limited (e.g., are not flexible and/or are fairly brittle), which limits use as a functional conductive component.

There is great interest in the field of additive manufacturing to develop improved materials that can be used to easily print completely integrated functional objects with limited post-assembly. This would allow completely new designs in the manufacturing and consumption of everyday objects, particularly when they can be enabled with conductive materials. The capability of printing conductive components within an object can provide the potential for embedded sensors and electronics.

Common techniques in additive manufacturing utilize the extrusion of molten polymer through a heated nozzle. This method is used in, for example, fused deposition modeling (FDM), where a filament is fed into a hot zone for continuous extrusion. The molten polymer can be deposited layer by layer onto a build plate in order to form three-dimensional (3D) objects. In addition to printing of plastic objects, there is strong interest in 3D printing of conductive materials and the use of additive manufacturing of structures containing electronic components. However, there are very few filament materials currently on the market which exhibit electrical conductivity, and those which are available have relatively low conductivities, which limits the range of potential applications. The materials are typically constructed such that one conductive material forms a percolating network through an insulating polymer base, such that electrons have a continuous pathway to flow. The formation of this conductive network is limited to the way the conductive particles are arranged within the polymer base. Although these materials have been extensively explored in both academia and industry, the focus is typically on minimizing the amount of conductive additive required to form a percolating network, where the conductivity is relatively low. One example of a paper directed to the study of electrical percolation is Yao Sun et al., Modeling of the Electrical Percolation of Mixed Carbon Fillers in Polymer-Based Composites, Macromolecules 2009, 42, 459-463, which describes the use of multi-walled carbon nanotubes and either carbon black or graphite to lower percolation thresholds for polymer composites. This paper does not describe techniques for increasing conductivity substantially beyond the percolation threshold. Nor does it discuss the use of conductive polymers for additive manufacturing.

Meanwhile, the field of 3D manufactured electronics allows for incorporation of function into objects. For example, structural electronics (SE) involves electronic and/or electrical components and circuits that act as load-bearing, protective structures. In the case of load bearing applications, electronic components may occupy space within an object or structure without creating new space, or may occupy a very limited amount of space so as to have a negligible effect on the structural stability and/or load bearing ability of the component.

The ability to predict structural failure of articles using structural electronics would be a welcome step forward in the art, and could have significant impacts in the field of additive manufacturing. The ability to modify the mechanical properties of the structural electronic materials to be a functional match to the structural material, with the mechanical robustness lessened by some defined amount, would provide a new technique in the art.

SUMMARY

In an embodiment, there is an article comprising a body and at least one 3D-printable conductive composite segment in mechanical communication with the body. The body comprises a first material and the at least one 3D-printable conductive composite segment comprises a matrix material, a plurality of carbon nanotubes, and a plurality of conductive additives. The conductive additives comprise a plurality of metallic particulates, a plurality of graphitic particles or a combination thereof.

In another embodiment, there is a method of forming an article. The method comprises forming a body and forming at least one 3D-printable conductive composite segment in mechanical communication with the body. The body comprises a first material and the at least one 3D-printable conductive composite segment comprises a matrix material, a plurality of carbon nanotubes, and a plurality of conductive additives. The plurality of conductive additives comprises metallic particulates, graphitic particles or a combination thereof.

In yet another embodiment, there is a method for monitoring structural integrity of an object. The method comprises measuring a conductivity value of at least one 3D-printable conductive composite segment that is in mechanical communication with body portion of an article; comparing the measured conductivity value to a known conductivity value; determining whether a difference between the measured conductivity value and the known conductivity value falls within a predetermined threshold value; and generating an alarm if the difference is within the predetermined threshold value. The 3D-printable conductive composite segment comprises a matrix material, a plurality of carbon nanotubes, and a plurality of conductive additives. The plurality of conductive additives comprises metallic particulates, graphitic particles or combinations thereof.

The 3D-printable conductive composites of the embodiments exhibit one or more of the following advantages: adjustable electrical conductivity and adjustable mechanical properties; increased usability such as for use in monitoring structural stability of articles, filaments for 3D printing applications, such as fused deposition modeling (FDM); an unexpected, synergistic increase in electrical conductivity when conductive additives such as metallic particulates and/or graphitic particles are added to multi-walled carbon nanotube/polymer composites; an improved method for increasing the electrical conductivity in composites while retaining material properties suitable for additive manufacturing.

It is to be understood that both the foregoing general description and the following detailed description are exemplary and explanatory only and are not restrictive of the present teachings, as claimed.

BRIEF DESCRIPTION OF THE DRAWINGS

The accompanying drawings, which are incorporated in and constitute a part of this specification, illustrates embodiments of the present teachings and together with the description, serve to explain the principles of the present teachings.

It should be noted that some details of the figure have been simplified and are drawn to facilitate understanding of the embodiments rather than to maintain strict structural accuracy, detail, and scale.

DESCRIPTION OF THE EMBODIMENTS

Reference will now be made in detail to embodiments of the present teachings, examples of which are illustrated in the accompanying drawings. In the drawings, like reference numerals have been used throughout to designate identical elements. In the following description, reference is made to the accompanying drawing that forms a part thereof, and in which is shown by way of illustration a specific exemplary embodiment in which the present teachings may be practiced. The following description is, therefore, merely exemplary.

Embodiments of the present disclosure are directed to conductive formulations such as composites that include carbon nanotubes (e.g., single and/or multi-walled carbon nanotubes) and further contain conductive additives, for example, metallic and graphitic materials, and which may be incorporated into articles such as for the purpose of indicating structural compromise or potential structural failure of the articles.

The term "conductive additive" is defined herein to include metallic particulates and/or graphitic particles. The term "metallic particulates" is defined herein to include metal structures in the form of metal wires, fibers, flakes and particles. The term "graphitic additives" is defined herein to include graphitic structures comprising graphite or graphene.

In an embodiment, a method of forming an article 112 comprises forming a body 120 and forming at least one conductive composite segment 123, which may be a 3D-printable conductive composite, in mechanical communication with the body 120. As used herein "mechanical communication" means configured in a manner such that a mechanical load exerted on the body is at least partially transferred to at least a portion of the conductive composite segment. As used herein "3D-printable" means capable of being extruded through and deposited by a nozzle of a 3D printer, for example, as described below. Accordingly, the conductive composite segment may be incorporated within the body, on a surface of the body or both.

Figure 1:
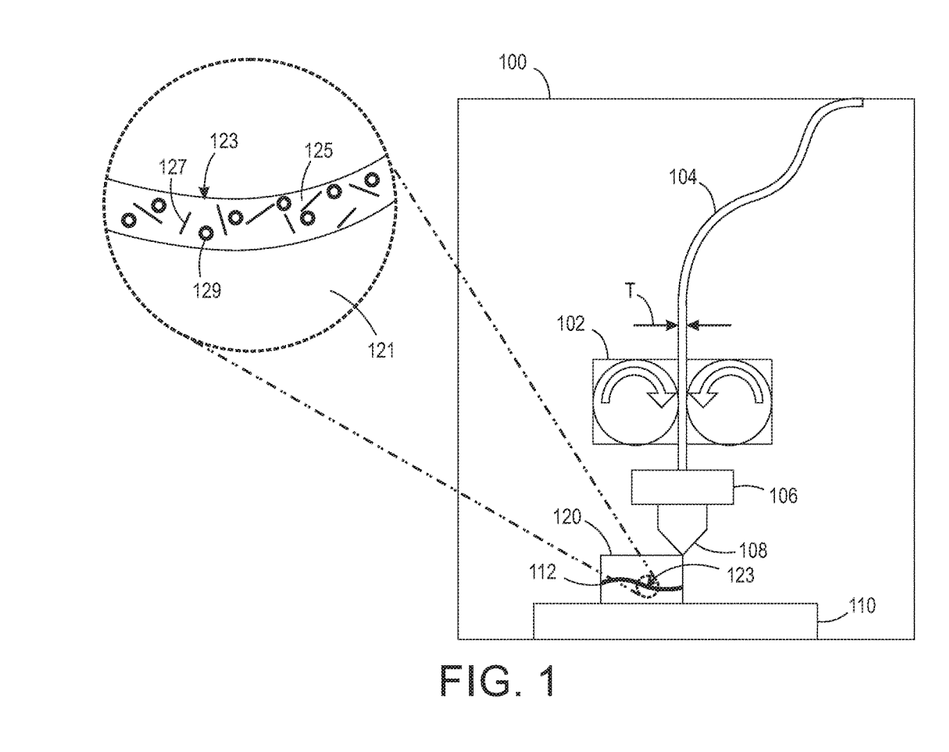
FIG. 1 illustrates a method of forming an article comprising a structural material and at least one 3D-printable conductive composite segment in mechanical communication with the structural material according to an embodiment.

While not limited to any particular embodiment, methods of the embodiments for forming an article may be performed via three-dimensional (3D) printing, for example, as illustrated in FIG. 1 which shows 3D printer 100 forming an article 112. The 3D printer 100 includes a feeder mechanism 102 for supplying a filament 104 to a liquefier 106. The liquefier 106 melts the filament 104 and the resulting melt is extruded through a nozzle 108 and deposited to form article 112, for example, on a build platform 110. The feeder mechanism 102 can comprise rollers or any other suitable mechanism capable of supplying the filament 104 from, for example, a spool of filament (not shown). The liquefier 106 can employ any technique for heating the filament, such as heating elements, lasers and so forth. The three dimensional printer 100 as shown in FIG. 1 is exemplary only and any type of three dimensional printer can be employed to deposit the filaments of the present disclosure. Alternatively, other methods known in the art may be utilized, including combinations of different fabrication methods. For example, all or portions of body 120 and all or portions of conductive composite segment 123 may be formed by the same process, within the same process, by different processes or a combination of processes including casting, extrusion, 3D printing. In fact, all or portions of body 120 and all or portions of conductive composite segment 123 may be formed in a continuous process, or may be formed in separate processes and assembled together in a subsequent process or process step.

The article 112 may comprise compositions provided by filament 104. Filament 104 may be a single continuous filament comprising the same composition throughout, a single continuous filament comprising different sections having different compositions, multiple filaments comprising the same composition or different filaments comprising different compositions. In this way, an article comprising a uniform composition throughout may be formed, or an article comprising different compositions (e.g., different sections thereof comprising different compositions) may be formed. For example, a first one of filament 104 (or a first portion of a continuous one of filament 104) may comprise a first composition, may be processed by the 3D printer and deposited to form the body 120 of article 112. Similarly, a second one of filament 104 (or a second portion of a continuous one of filament 104) may comprise a second composition, may be processed by the 3D printer and deposited to form conductive segment 123. Accordingly, an article 112 comprising body 120 and the at least one conductive composite segment 123 in mechanical communication with the body may be formed.

In the article 112 shown in FIG. 1, the body comprises a first material 121 and the at least one conductive composite segment 123 comprises a matrix material 125, a plurality of carbon nanotubes 127, and a plurality of conductive additives 129. The conductive additives in the conductive composite 123 comprise a plurality of metallic particulates, a plurality of graphitic particles or a combination thereof.

The composition of conductive composite segment 123 may be selected according to its conductive and/or mechanical properties. The conductive composite segment may have a bulk conductivity greater than 1 S/cm, such as greater than 3 S/cm, such as greater than 3.5 S/cm or greater than 4 S/cm. Bulk conductivity is calculated using the formula, $$\sigma = L/(R*A) \quad (1)$$

Where:
σ is bulk electrical conductivity;
L is length of the filament;
R is measured resistance of a conductive composite segment;
A is the cross-sectional area ($\pi r^2$) of the filament, where r is the radius of the conductive composite segment.

The resistance, R, can be measured by forming an conductive composite segment, such as via extrusion or 3D printing. The ends/tips of the conductive composite segment may placed in electrical connections with testing equipment (e.g., a digital multimeter). Resistance can then be measured across the length of the conductive composite segment. The dimensions of the conductive composite segment and the measured value for R can then be used to calculate bulk conductivity (σ) of the composite. While not limited to any particular theory, it is believed that most of the resistance in the conductive composite segment of the embodiments results from tunneling between local conductive networks and the use of high aspect ratio carbon nanotubes (e.g., MWCNTs) which act as effective networked bridges across insulating portions of the matrix material. The additional conductive additives, which do not form percolating networks on their own, provide an unexpected boost in conductivity.

The conductive composites of the present disclosure, such as the 3D-printable conductive composite of an embodiment, can be made by any suitable method. For example, a thermoplastic polymer can be combined with carbon nanotubes and at least one conductive additive using melt mixing techniques. Other suitable techniques for mixing such compositions are well known in the art.

The ability to adjust the mechanical properties of the conductive composites of the embodiments allows for a complimentary match of mechanical properties between the structural materials of an article and the conductive composite material, such as a conductive composite material segment mechanically coupled to the article. In an embodiment, the conductive composite does not have equivalent mechanical properties to the structural material such as that used for a body of an article, and in other embodiments the conductive composite is less robust than the structural material. The difference in robustness between the conductive composite and the structural material may be determined based on a given need or application. When the consideration of safety is paramount, it is desirable that the conductive composite is much less robust, and therefore indicates the possibility of a stress event, such as failure and/or the presence of small defect already formed at an earlier stage in the functional life of the article. If it is desirable to predict failure just before an the stress event, or during a stress event, the conductive composite may have near equivalent or equivalent properties to the structural material. Therefore, as mentioned above, the body 120 may comprise a first composition and the conductive composite 123 may comprise a second composition. However, the first composition and the second composition may comprise the same or different compositions. For example, body 120 may comprise a first material 121 which is the same or different than matrix material 125 of the conductive composite segment 123. In an example, the matrix material 125 and the first material 121 may comprise the same or different materials. For example, the matrix material 125, first material 121, or both may comprise a thermoplastic polymer. Generally, combinations of the first material 121 and matrix material are not limited so long as a breaking strain of the conductive composite 123 is equal to or lower than a breaking strain of the body 120. Thus, for example, the first material may comprise concrete and the matrix material of the conductive composite segment may comprise a thermoplastic polymer.

Figure 2A:
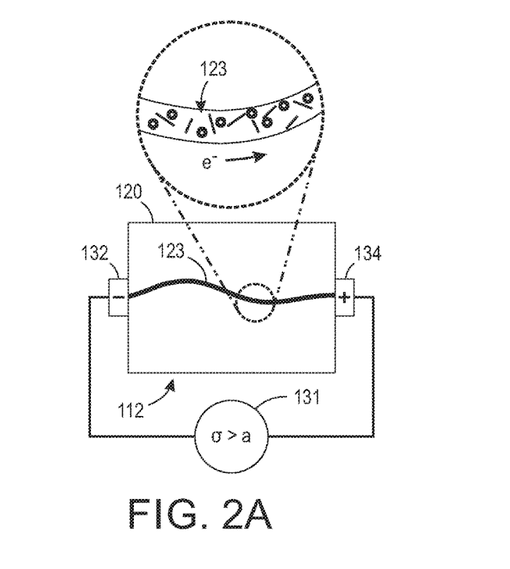
FIGS. 2A-2B illustrates how a stress event leads to a change or loss in conductivity across a 3D-printable conductive composite segment in the article of FIG. 1. The stress event may be monitored via changes in conductivity as an early indication of an oncoming failure event, such as a developing crack in the article.
Figure 2B:
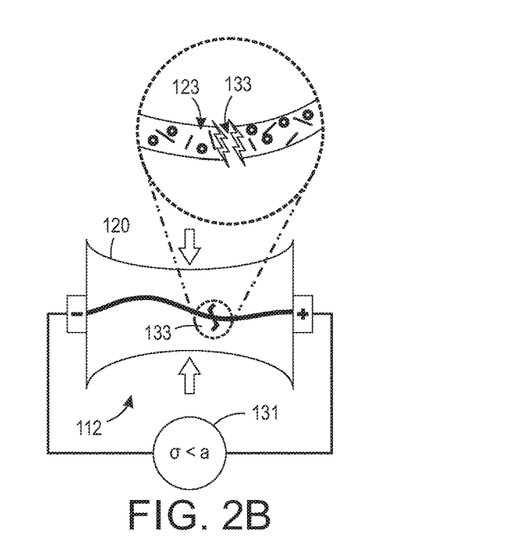
Figure 3:
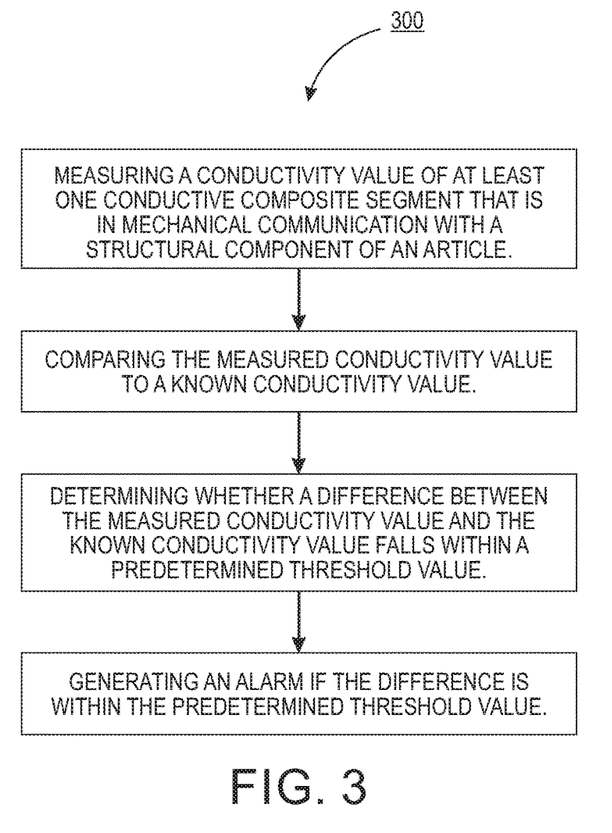
FIG. 3 illustrates a method for monitoring structural integrity of an article, such as the article of FIG. 1 as it undergoes a stress event as illustrated in FIGS. 2A-2B.

As described above, the robustness of the conductive composite relative to structural materials of the article may be selected based on need or application. Accordingly, the conductive composite 123 may have a breaking strain that is equal to or less than a breaking strain of the body 120 so that it may experience mechanical failure before body 120 experiences mechanical failure, which is useful in applications such as monitoring structural integrity of objects. A mechanical failure is illustrated by FIGS. 2A-2B in which an article 112 is exposed to a mechanical load (indicated by the upward and downward pointing arrows). Such a mechanical load can otherwise result in the formation of cracks at weak points of the article which may then propagate and damage article 112. However, if conductive composite segment 123 has a breaking strain that is equal to or lower than that of body 120, cracks may preferentially form in conductive composite segment 123 and propagate in a manner so as to lower the segment's conductivity. For example, in FIG. 2A, an electric current (indicated by flow direction of electron "e⁻" is generated across conductive composite segment 123 via electrical communication with electrodes 132 and 134. That is, conductive composite segment 123 may be incorporated in article 120 as a conductive wire. A conductivity "σ" of the conductive composite segment 123 may be determined to be greater than a value "a". Then, as article 112 is exposed to a stress event (such as a mechanical load), crack 133 forms at segment 123. The crack may propagate in a manner to reduce the conductivity of segment 123 to a value lower than "a", or may result in loss of conductivity across segment 123. Accordingly, conductive composite segment 123 may be incorporated with a failure sensor 131 that is used for monitoring structural integrity of an article. For example, sensor 131 may be configured to generate signals corresponding to a sensed conductivity of conductive composite segment 123 with which it is in electrical communication, and the signals may be provided to a computer (not shown) which then analyzes the signals. In an embodiment, the computer includes a processor that executes instructions for analyzing the signals. For example, the instructions executed by the processor may be for a method 300 for monitoring structural integrity of an object and may include: measuring a conductivity value of at least one conductive composite segment that is in mechanical communication with body portion of an article; comparing the measured conductivity value to a known conductivity value; determining whether a difference between the measured conductivity value and the known conductivity value falls within a predetermined threshold value; and generating an alarm if the difference is within the predetermined threshold value. As described above, such a conductive composite may be a 3D-printable conductive composite, and may include a matrix material, a plurality of carbon nanotubes and a plurality of conductive additives comprising metallic particulates, graphitic particles or combinations thereof.

First Material

As described above, the first material and the matrix material of the conductive composite segment may be the same material. Accordingly the first material may be a 3-D printable material. Exemplary ones of the first material include concrete, metal, plastic (polymer) such as a thermoplastic polymer. For example, the first material may be any structural material that is used in bridges, building foundations, and supporting columns or any material that may be exposed to loads that over time might cause formation and propogation of cracks therethrough. The first material may be the same material or a different material than the matrix material of the conductive polymer composite. Accordingly, materials described below for the matrix material may also be applicable for the first material.

Exemplary polymeric first materials may be those which are commonly printed by filament extrusion printing techniques include polycaprolactone, estane, polylactic acid, acrylonitrile butadiene styrene, nylon, polycarbonate, acrylonitrile styrene acrylate or mixtures thereof.

Matrix Material

The matrix material 125 may comprise a polymeric material. For example, the matrix material 125 may comprise a thermoplastic polymer. The thermoplastic polymer of matrix material 125 may be the same or different than the thermoplastic polymer of first material 121. Accordingly, materials described above for the first material may also be applicable for the matrix material.

Any suitable thermoplastic polymer useful in three dimensional printing can be employed as the first material 121 of body 120 or as the matrix material 125 of conductive composite 123. The first material 121 and/or the matrix material 125 may include a single polymer or mixtures of thermoplastic polymers, including mixtures of any of the thermoplastic polymers disclosed herein. In an embodiment, the thermoplastic polymer comprises at least one repeating unit selected from the group consisting of acrylate units, carboxylic acid ester units, amide units, lactic acid units, benzimidazole units, carbonate ester units, ether units, sulfone units, arylketone units, arylether units, etherimide units, ethylene units, phenylene oxide units, propylene units, styrene units, vinyl halide units and carbamate units. In an embodiment, the thermoplastic polymer is a copolymer, such as a block copolymer, of two or more of any of the above listed repeating units. As an example, the thermoplastic polymer can comprise at least one polymer selected from the group consisting of polyacrylates, polybenzimidazoles, polycarbonates, polyether sulfones, polyaryl ether ketones such as polyether ether ketone, polyetherimide, polyethylenes such as polyethylene and poly(ethylene-co-vinylacetate), polyphenylene oxides, polypropylenes such as polypropylene and Poly(vinylidene fluoride-co-hexafluoropropylene), polystyrenes such as polystyrene, poly(styrene isoprene styrene), acrylonitrile butadiene styrene (ABS) and poly(Styrene Ethylene Butylene Styrene) (SEBS), polyesters such as polyethylene terephthalate, polylactic acid (PLA) and polycaprolactone, polyurethanes, polyamides such as nylon, Poly(vinylidene fluoride) (PVDF) and polyvinyl chlorides. In an embodiment, the thermoplastic polymer does not include Acrylonitrile butadiene styrene (ABS) or PLA.

In an embodiment, the thermoplastic polymer is a selected from the group consisting of polyacrylates and copolymer of acrylates, such as block copolymers of acrylates. The acrylate copolymers can comprise at least one acrylate monomer and optionally one or more additional monomers such as any of those monomers listed above for use in the thermoplastic polymers. Such polymers can be formulated to have a desired degree of flexibility. In an embodiment, the polymer can be a polyester, such as polycaprolactone.

The thermoplastic polymer can be included in the composite in any suitable amount that will allow the composite to function in a three dimensional printing process. Examples of suitable amounts include a range of from about 10% to about 90% by weight, such as about 40% to about 70%, or about 40% to about 60%, relative to the total weight of the conductive polymer composite. The composite can include carbon nanotubes and a plurality of metallic particulates in any suitable amount that will provide the desired conductivity.

Carbon Nanotubes

Any suitable carbon nanotubes can be employed in the embodiments. Examples of suitable carbon nanotubes include single walled carbon nanotubes (SWCNT), multi-walled carbon nanotubes (MWCNTs) and mixtures thereof. In an embodiment, the carbon nanotubes are MWCNTs. Commercially available sources of carbon nanotubes include, for example, carbon nanotubes available from CHEAPTUBES™ or NANOCYL™, such as Nanocyl 7000.

Example amounts of carbon nanotubes include a range of from 1% to about 20% by weight, such as about 3% to about 15% by weight, or about 5% to about 10% by weight, relative to the total weight of the conductive composite used for forming the conductive composite segment 123. Larger amounts of carbon nanotubes may reduce processability of the composition by a 3D printer, depending, on among other things, the type of thermoplastic and the printing process employed. Thus, in an embodiment, carbon nanotube concentrations of 20% by weight or less, such as 10% by weight or less, may be preferred.

Conductive Additives

Conductive additives may be selected from metallic particulates, graphitic particles or a combination thereof. Example amounts of conductive additives include a range of from about 1% to about 50% by weight, such as about 10% to about 40% by weight, or about 20% to about 30% by weight, relative to the total weight of the conductive composite used for forming the conductive composite segment 123.

Metallic Particulate

Any suitable metallic particulates can be employed in the conductive composite of the present disclosure. The metallic particulates can be selected from one or more forms such as metallic flakes, metallic particles, metallic wires and mixtures of metallic flakes, metallic particles and metallic wires. The plurality of metallic particulate may comprise particulates that are defined by at least one dimension, for example, a diameter, that may be in a range of from about 50 nm to about 5 μm. In some embodiments the metal particulates may have one of its dimensions in a range of less than or equal to about 100 nm. Therefore, the plurality of metallic particulates may comprise a plurality of metal particulates comprising nanoparticulates and/or micron-scale particulates. For example, the plurality metallic particulates may comprise metal additives in the form of a plurality of metal wires, including nanowires and/or micron-scale wires; a plurality of flakes, including nanoflakes and/or micron-scale flakes; and/or a plurality of particles, including nanoparticles and/or micron-scale particles. In an example, the metal wires may have an aspect ratio that is higher than an aspect ratio of the metal flakes, and the metal flakes may have an aspect ratio that is higher than an aspect ratio of the metal particles. In addition to increasing the conductivity of the composites in which they are incorporated, the conductive additives may also serve as fillers that can significantly impact the brittleness of the resulting conductive composite material.

For the metal particulates, any suitable metal additive useful in three-dimensional printing can be employed in the composites of the present disclosure. The metal may be selected from any metal and may include metal alloys. Any suitable metal can be employed, for example, in any particular form. Examples of suitable metals include Bi, Sn, Sb, Pb, Ag, In, Cu, or alloys thereof. For example, alloys may include at least one of the following, BiSnPb, BiSn, BiSnAg, SbPbBi, SnBi, InSn, SnInAg, SnAgCu, SnAg, SnCu, SnSb, SnAgSb, or mixtures thereof. One embodiments of a metal alloy includes Indalloy #282 (IND-282), available from INDIUM CORPORATION®, United States).

Example amounts of metal particulates include a range of from about 1% to about 50% by weight, such as about 10% to about 40% by weight, or about 20% to about 30% by weight, relative to the total weight of the conductive composite used for forming the conductive composite.

Graphitic Particles

Any suitable graphitic particles can be employed in the composites of the present disclosure. The graphitic particles can be selected from structures including graphene particles, graphite particles and mixtures of graphene particles and graphite particles.

Commercially available sources of graphitic particles include, for example, graphite powder available from Cabot Corporation (Billerica, Mass.), or Sigma Aldrich Corporation (St. Louis, Mo.), and/or graphene available from Graphenea (Cambridge, Mass.), Graphene Industries (Manchester, UK), size 5 μm graphene nanoplatelets grade M available from XG Sciences, Inc. (Lansing Mich.) but may also be selected from graphene ranging in sizes from about 1 μm to about 100 μm, for example from about 1 μm to about 40 μm, including from about 1 μm to about 5 μm.

Example amounts of graphitic particles include a range of from about 1% to about 50% by weight, such as about 10% to about 40% by weight, or about 20% to about 30% by weight, relative to the total weight of the conductive composite used for forming the conductive composite.

The conductive composites of the present disclosure can include any other suitable optional ingredients in any desired amounts, such as carrier liquids, plasticizers, dispersants and surfactants. Alternatively, ingredients not expressly recited in the present disclosure can be limited and/or excluded from the conductive polymer composites disclosed herein. Thus, the amounts of the thermoplastic polymer, carbon nanotubes and conductive additives, with or without any optional ingredients can add up to 90% to 100% by weight of the total ingredients employed in the composites of the present disclosure, such as 95% to 100% by weight, or 98% to 100% by weight, or 99% to 100% by weight, or 100% by weight of the total ingredients.

The present disclosure is also directed to a method of three dimensional printing. Any type of three dimensional printing can be employed, such as filament printing (e.g., FDM) or paste extrusion. The method includes providing any a composite to a three dimensional printer. The composite can be in any suitable form useful in three dimensional printing, such as a filament or paste. The conductive polymer can be heated to a molten state suitable for extrusion. Then the heated conductive polymer is extruded onto a substrate to form a conductive composite segment in mechanical communication with a body of an article.

The conductive composites of the present disclosure can be used in a FDM process by first forming the composite into a conductive composite segment having a desired shape and dimensions (e.g., by extrusion or any other suitable process). The conductive composite segment can have any suitable shape that will allow the segment to placed in mechanical communication with the body of an article.

Filaments used for forming articles of the embodiments, as initially supplied, can have a continuous length that is much longer than its thickness, T, (shown in FIG. 1) such as a ratio of length to thickness that is greater than 100 to 1, such as greater than 500 to 1 or 1000 to 1 or more, where T is the smallest thickness dimension of the filament (e.g., the diameter if the filament has a circular cross-section). Any suitable thickness can be used, and may depend on the 3D printer being used. As an example, thicknesses can range from about 0.1 mm to about 10 mm, such as about 0.5 mm to about 5 mm, or about 1 mm to about 3 mm.

While not limited to any particular use, the conductive composite segments of the embodiments may be used in several applications including for monitoring large objects such as bridges, building foundations and main supports, as well as tanks or containers containing chemicals or oil. For example, electronic indicators comprising the conductive composite segments of the embodiments may be placed in areas particularly expected to be weak points in any article. Middle sized object applications in which the conductive composite segments of the embodiments may be incorporated include aerospace and structural components, such as a rotor or airplane wing. Smaller sized objects in which the conductive composite segments of the embodiments may be incorporated include bicycles and safety equipment including baby car seats.

EXAMPLES

Example 1

Conductive composites segments were prepared by melt mixing a polymer base (Polycaprolactone; "PCL") with 10% by weight of multi-walled carbon nanotubes (MWNT) along with 30% by weight silver (Ag) flakes on a Haake twin-screw extruder for 30 minutes at 30 rpm. The resulting material was cryogenically ground and the ground composite was extruded into a filament using a Melt Flow Indexer (MFI) and a modified die. The conditions for extrusion on the MFI included a 1.8 mm orifice and 16.96 kg weight in order to prepare final filament. The final filament had a diameter of about 1.75 mm.

Example 2

10 cm section of the extruded filament of Example 1, with ends painted in silver paint, were used to measure resistance in order to calculate bulk conductivity. Resistance measurements were completed using a digital multimeter. Bulk conductivity was calculated using formula 1 above.

Example 3

A composite similar to that of Example 1 was made, but with 30% by weight Ag nanoparticles instead of Ag flakes.

Example 4

A composite similar to that of Example 1 was made, but with 30% by weight IND-282 particles instead of the silver flakes.

Example 5

A composite similar to that of Example 1 was made, but with 26% by weight copper wire instead of the silver flakes.

Example 6

A composite similar to that of Example 1 was made, but with 10% by weight graphite instead of the silver flakes.

Example 7

A composite similar to that of Example 1 was made, but with 30% graphene instead of the silver flakes.

Example 8

A composite similar to that of Example 1 was made, but with 30% by weight of Tungsten wire instead of the silver flakes.

Example 9

A composite similar to that of Example 1 was made, but with 30% by weight of graphite instead of the silver flakes.

Comparative Example A

A composite similar to that of Example 1 was made, but without the silver flakes.

Bulk conductivity was measured for each of the examples 3-9 and Comparative Example A in a manner similar to that described for Example 2. Results are shown in FIG. 4.

It is noted that for the conductive composite segments formed according to Examples 7 and 9 showed conductivities of about 3.9 S/cm and about 4.2 S/cm respectively. Meanwhile, the conductive composite segments formed according to Examples 4 showed a conductivity of 0.05 S/cm and the 10% by weight MWNT carbon nanotube concentration in Comparative Example A resulted in a conductivity of 0.5 S/cm, which is well above the percolation threshold and is a significantly higher conductivity than any material or combination thereof known for hot extrusion additive manufacturing. Thus, as in some of the other examples, the conductive additives were added to a MWNT-polymer system that has already reached its percolation threshold.

Figure 4:
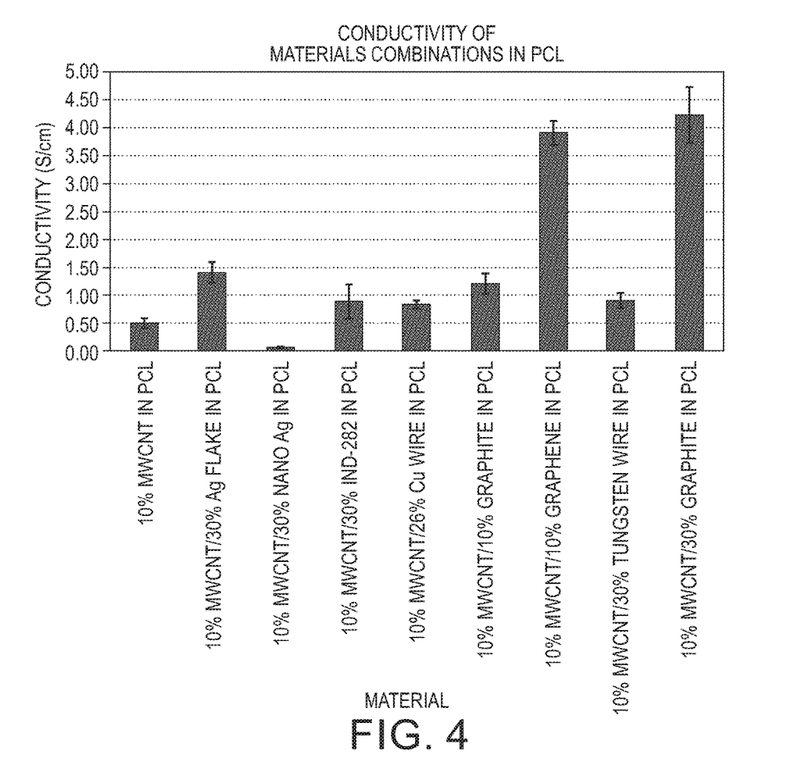
FIG. 4 shows a synergistic effect on conductivity of 3D-printable conductive composites comprising multi-walled carbon nanotubes and conductive additives in a thermoplastic polymer base (polycaprolactone) (PCL), according to an example of the present disclosure. The percentages of carbon nanotubes and conductive additives are shown in wt % relative to a total weight of the 3D-printable conductive composite.

From the results for graphite particles in FIG. 4, it is evident that the combination of MWNT and graphite particles had a synergistic effect when combined with one another in a plastic composite, since the combination had a much higher conductivity than each of the components on their own. The results for BiSnAg alloy particles with the MWNT in the plastic composite, such as that for Example 4, show a similar synergistic effect in FIG. 4, as did the results for copper wire and tungsten wire in the MWNT/plastic composite such as in Examples 5 and 8, respectively, as well as the results for copper wire in Examples 6. With 30% graphite/10% MWNT loading, the conductivity was significantly higher compared with the 10% graphite/10% MWNT loading. Such a large increase in conductivity would not have been expected.

It was not expected that a synergistic increase in conductivity would occur for the Example compositions of FIG. 4 for several reasons. The conductive additives on their own in a plastic composite (i.e., without the MWNTs), such as in the comparative examples, have significantly lower, such as about zero, conductivity. Also, it was not evident that the increase in conductive additive loading would result in such a drastic increase in conductivity in the conductive at the carbon nanotube concentrations employed.

Thus, the data of FIG. 4 demonstrates that an unexpected nonlinear increase in conductivity was observed upon addition of at least one conductive additive, which evidences a synergistic effect of the combination carbon nanotubes and conductive additives at relatively high loadings. The synergistic increase in electrical conductivity is unexpected because the selected ones of the at least one conductive additive do not form percolating networks with loadings as high as 35-50 wt %. These metallic additives do, however, contribute to the existing percolating network formed by the carbon nanotubes. This synergistic increase provides an additional advantage in the case of additive manufacturing because increasing the loading of a single particle would not be an effective method for increasing the conductivity. In the case of MWNT, for example, a maximum loading of about 20% by weight is reached where the composite it no longer processable for additive manufacturing. At this loading the melt flow temperature exceeds the capabilities of current technologies.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein.

Example 10

Figure 5:
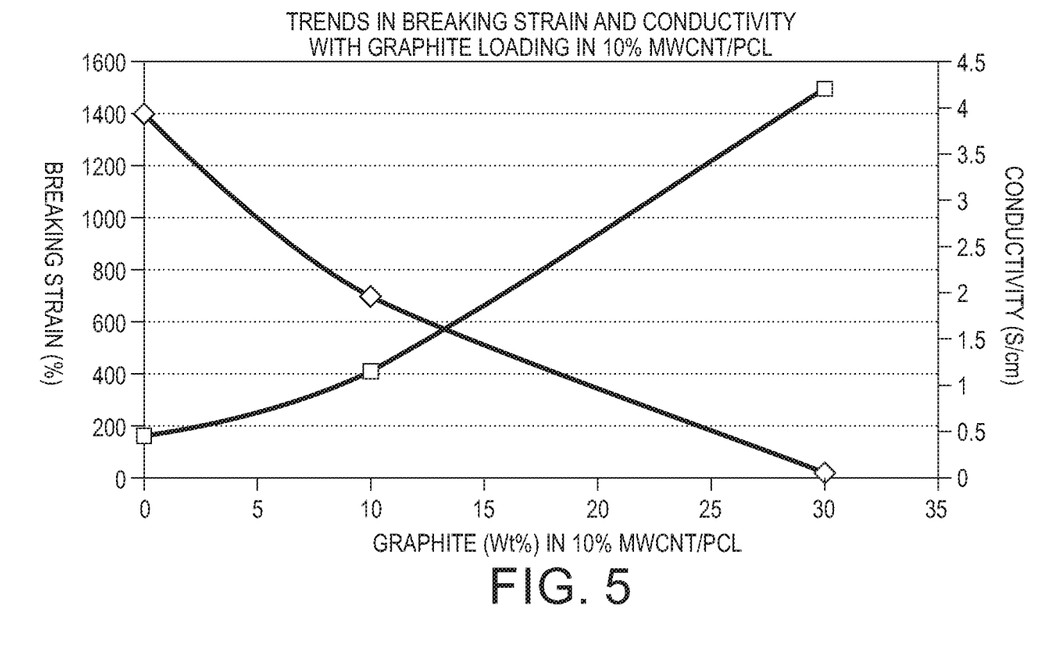
FIG. 5 shows trends in breaking strain and conductivity of one of the composites of FIG. 4 comprising various loading levels of graphite in a carbon nanotube/PCL composite.

Bulk conductivity was measured for conductive composite compositions comprising 10% MWCNT/graphite/PCL at various loadings of the graphite with the results shown in FIG. 5. This example shows that it is possible to control conductivity coupled with brittleness. For example, at 10% MWCNT in PCL, the breaking strain declines (brittleness increases) and so does conductivity with the addition of graphite.

Comparative Example B

A base material segment made from only PCL (no carbon nanotubes and no conductive additives) was prepared.

Example 10

A composite segment comprising poly(SIS), 10% MWCNT and 30% graphene was prepared.

Comparative Example C

A base material segment made from only poly(SIS) (no carbon nanotubes and no conductive additives) was prepared.

Example 11

A composite segment comprising poly(SIS), 10% MWCNT and 30% graphene was prepared.

Comparative Example D

A base material segment made from only estane (no carbon nanotubes and no conductive additives) was prepared.

Example 12

A composite segment comprising estane, 10% MWCNT and 30% graphene was prepared.

Example 13

Figure 6:
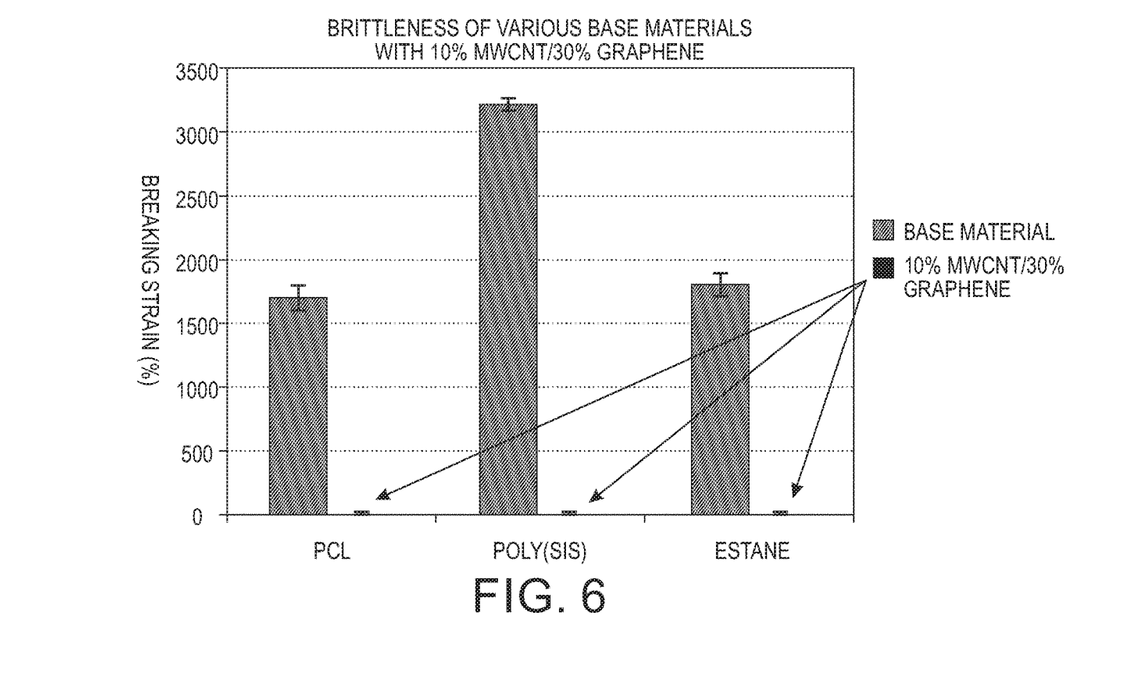
FIG. 6 is a graph comparing trends in brittleness (breaking strain %) of composites comprising multiwalled carbon nanotubes (at 10 wt %) and graphene in various base materials

Breaking strain was measured for the composites of Examples 10-12 and the base materials of comparative Examples B-D. The results are shown in FIG. 6 and indicate that 10% MWCNT/30% graphene in various base materials have the same brittle characteristics as in PCL Example 14

A 10×10×100 mm rectangular object was printed using a MakerBot Replicator 2X dual extruder printer, available from Makerbot Industries (Brooklyn, N.Y.). The object comprised a body that was 3D printed using Ninjaflex composite thermoplastic polyurethane resin material available from NINJATEK™ (Manheim, Pa.), and a conductive composite segment comprising a 10% MWCNT/30% Graphene/polycaprolactone composite material, for example, as described for Example 7 above. The conductive composite segment was 3D printed internally through the object. It was observed that for the conductive composite of Example 14, the graphitic material increased brittleness causing it to be mechanically weak. The conductive segment extended through the object and had dimensions of 2×2×100 mm and included protruding contacts at each end of the object.

Silver paint was applied to the protruding contacts at each end of the object, and the ends were additionally wrapped with copper tape. Alligator clips were attached for measurement of current with a benchtop multimeter for conversion to conductivity values.

Comparative Example E

A 10×10×100 mm rectangular object was printed using the MakerBot Replicator 2X dual extruder printer. The object comprised a body that was 3D printed using Ninjaflex composite thermoplastic polyurethane resin material available from NINJATEK™ (Manheim, Pa.) and a conductive composite segment comprising a 10% MWCNT/polycaprolactone composite material that did not comprise any conductive additives, for example, as described for Comparative Example A above. A conductive composite segment was 3D printed internally through the object. The conductive segment extended through the object and had dimensions of 2×2×100 mm and included protruding contacts at each end of the object. The conductive segment was observed to be more flexible than the conductive segment of Example 14.

Silver paint was applied to the protruding contacts at each end of the object, and the ends were additionally wrapped with copper tape. Alligator clips were attached for measurement of current with a benchtop multimeter for conversion to conductivity values.

Example 15

Figure 7:
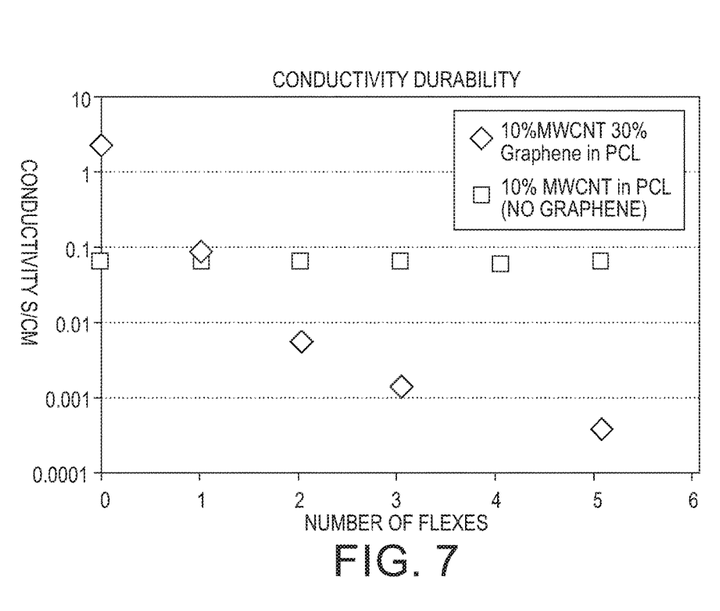
FIG. 7 is a graph comparing conductivity durability of 3D-printed composites used as conductive lines through 3D printed polymeric articles.

The objects of Example 14 and Comparative Example E were subjected to three point flex-testing in order to simulate a stress event and the conductivities of their respective conductive composite segments were monitored during testing. For example, conductivities of the conductive composite segments of each object were recorded after each flex as shown in FIG. 7 The conductivity plots of FIG. 7 shows boundary cases for the conductivity of the conductive composite in the object of Example 14 (with the conductive composite comprising 10% MWCNT/30% Graphene in PCL) and of the conductive composite in the object of Comparative Example E (with the conductive composite comprise 10% MWCNT in PCL and no conductive additives). For each flex during the flex-testing of the object of Example 14, the measured conductivity value of its conductive composite segment decreased. While not limited to any particular theory, it is believed that early-stage stress events can, therefore, be monitored by measuring changes in conductivity of a conductive composite having conductive additives because such conductive additives not only provide for a synergistic increase in starting conductivity but also result in a more brittle material, that experiences sharper declines of conductivity when stressed. For example, before any flex-testing, conductivity of the conductive segment of the Example 14 object (comprising the 10% MWCNT/30% Graphene/polycrapolactone conductive composite) was measured as 2.3 S/cm, which is in line with conductivity of the "brittle" conductive material. A flexure strain of about 2.95 mm deflection and 9.76 mm sample depth was then applied to the object. Conductivity was immediately and dramatically reduced to 0.09 S/cm after one flex, and diminished to $3 \times 10^{-4}$ S/cm (~0) after 5 flexes as shown in the graph of FIG. 7.

Meanwhile, the conductive composite of Comparative Example E was observed to be more flexible material and its conductivity remained substantially constant after each flex during the flex test. While not limited to any particular theory, it is believed that stress events having a range of magnitudes, terms, frequencies can, therefore, be monitored by adjusting the mechanical properties of a conductive composite segment disposed in an article relative to the mechanical properties of the article body's structural material and monitoring conductivity of the composite segments for unexpected changes or changes greater than a predetermined tolerance from an expected or reference value.

While the present teachings have been illustrated with respect to one or more implementations, alterations and/or modifications can be made to the illustrated examples without departing from the spirit and scope of the appended claims. In addition, while a particular feature of the present teachings may have been disclosed with respect to only one of several implementations, such feature may be combined with one or more other features of the other implementations as may be desired and advantageous for any given or particular function. Furthermore, to the extent that the terms "including," "includes," "having," "has," "with," or variants thereof are used in either the detailed description and the claims, such terms are intended to be inclusive in a manner similar to the term "comprising." Further, in the discussion and claims herein, the term "about" indicates that the value listed may be somewhat altered, as long as the alteration does not result in nonconformance of the process or structure to the illustrated embodiment. Finally, "exemplary" indicates the description is used as an example, rather than implying that it is an ideal.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompasses by the following claims.

What is claimed is:

1. An article comprising:
  a body portion comprising a first material; and
  at least one 3D-printable conductive composite segment in mechanical communication with the body, the at least one conductive composite segment comprising
    a matrix material comprising a thermoplastic polymer,
    a plurality of carbon nanotubes; and
    a plurality of conductive additives comprising metallic particulates, graphitic particles or a combination thereof,
  wherein the thermoplastic polymer is present in an amount ranging from about 10% to about 90% by weight relative to the total weight of the conductive composite segment.

2. The article of claim 1, wherein the first material and the matrix material are the same material.

3. The article of claim 1, wherein the first material and the matrix material are different materials.

4. The article of claim 1, wherein the first material comprises concrete and the matrix material comprises a polymer.

5. The article of claim 1, wherein a breaking strain of the conductive composite is equal to or lower than a breaking strain of the body.

6. The article of claim 1,
  wherein the thermoplastic polymer comprises at least one polymer selected from the group consisting of polyacrylates, polybenzimidazoles, polycarbonates, polyether sulfones, polyaryl ether ketones, polyethylenes, polyphenylene oxides, polypropylenes, polystyrenes, polyesters, polyurethanes, polyamides, poly(vinylidene fluoride) (PVDF) and polyvinyl chlorides, polyether ether ketone, poly(ethylene-co-vinylacetate), polyetherimide, polypropylene, Poly(vinylidene fluoride-co-hexafluoropropylene), poly(styrene isoprene styrene), acrylonitrile butadiene styrene (ABS), poly(Styrene Ethylene Butylene Styrene) (SEBS), polyethylene terephthalate, polylactic acid (PLA), polycaprolactone and nylon.

7. The article of claim 1, wherein the carbon nanotubes comprise multi-walled carbon nanotubes and wherein the carbon nanotubes are present in an amount ranging from about 1% to about 20% by weight, relative to the total weight of the conductive polymer composite.

8. The article of claim 1, wherein the plurality of metallic particulates comprise one or more form selected from the group consisting of nanoflakes, nanoparticles and nanowires, and wherein the metallic particulates are present in an amount ranging from about 1% to 50% by weight, relative to the total weight of the conductive polymer composite.

9. The article of claim 1, wherein the plurality of the graphitic particles comprise at least one material selected from the group consisting of graphene and graphite, and wherein the plurality of the graphitic particles are present in an amount ranging from about 1% to about 50% by weight, relative to the total weight of the conductive polymer composite.

10. A method of forming an article comprising,
  forming a body comprising a first material; and
  forming at least one 3D-printable conductive composite segment in mechanical communication with the body, wherein the at least one conductive composite segment comprises
    a matrix material comprising a thermoplastic polymer,
    a plurality of carbon nanotubes; and
    a plurality of conductive additives comprising metallic particulates, graphitic particles or a combination thereof,
  wherein the thermoplastic polymer is present in an amount ranging from about 10% to about 90% by weight relative to the total weight of the conductive composite segment.

11. The method of claim 10, wherein the forming of the first material, the forming of the at least one conductive composite, or both, is by 3D printing.

12. The method of claim 10, wherein the first material and the matrix material are the same material.

13. The method of claim 10, wherein the first material and the matrix material are different materials.

14. The method of claim 10, wherein the first material comprises concrete and the matrix material comprises a polymer.

15. The method of claim 10, wherein a breaking strain of the conductive composite is equal to or lower than a breaking strain of the body.

16. The method of claim 10,
  wherein the thermoplastic polymer comprises at least one polymer selected from the group consisting of polyacrylates, polybenzimidazoles, polycarbonates, polyether sulfones, polyaryl ether ketones, polyethylenes, polyphenylene oxides, polypropylenes, polystyrenes, polyesters, polyurethanes, polyamides, poly(vinylidene fluoride) (PVDF) and polyvinyl chlorides, polyether ether ketone, poly(ethylene-co-vinylacetate), polyetherimide, polypropylene, Poly(vinylidene fluoride-co-hexafluoropropylene), poly(styrene isoprene styrene), acrylonitrile butadiene styrene (ABS), poly(Styrene Ethylene Butylene Styrene) (SEBS), polyethylene terephthalate, polylactic acid (PLA), polycaprolactone and nylon.

17. The method of claim 10, wherein the carbon nanotubes comprise multi-walled carbon nanotubes and wherein the carbon nanotubes are present in an amount ranging from about 1% to about 20% by weight, relative to the total weight of the conductive polymer composite.

18. The method of claim 10, wherein the plurality of metallic particulates comprise one or more form selected from the group consisting of nanoflakes, nanoparticles and nanowires, and wherein the metallic particulates are present in an amount ranging from about 1% to 50% by weight, relative to the total weight of the conductive polymer composite.

19. The method of claim 10, wherein the plurality of the graphitic particles comprise at least one material selected from the group consisting of graphene and graphite, and wherein the plurality of the graphitic particles are present in an amount ranging from about 1% to about 50% by weight, relative to the total weight of the conductive polymer composite.

20. A method for monitoring structural integrity of an object, comprising:
    providing an article having at least one 3D printable conductive composite segment that is in mechanical communication with a body of the article, wherein the at least one conductive composite segment comprises
        a matrix material comprising a thermoplastic polymer, wherein the thermoplastic polymer is present in an amount ranging from about 10% to about 90% by weight relative to the total weight of the conductive composite segment,
        a plurality of carbon nanotubes, and
        a plurality of conductive additives comprising metallic particulates, graphitic particles or combinations thereof;
    measuring a resistance value of the conductive composite segment cross an entire length of the conductive composite segment;
    calculating a conductivity value to determine a known conductivity value of the conductive composite segment;
    exposing the article to a stress event and measuring the resistant value of the conductive composite segment to determine changes in conductivity value during the stress event;
    comparing the measured changes in conductivity value during the stress event to the known conductivity value;
    determining whether a difference between the measured conductivity value and the known conductivity value falls within a predetermined threshold value that signifies a decrease in structural integrity of the body; and
    generating an alarm if the difference is within the predetermined threshold value.

* * * * *